US008153058B2

(12) United States Patent
Araiza et al.

(10) Patent No.: US 8,153,058 B2
(45) Date of Patent: Apr. 10, 2012

(54) DEVICE FOR THE TREATMENT OF A LIQUID OR GASEOUS MEDIUM BY MEANS OF UV RADIATION

(76) Inventors: Rafael Araiza, Walchwil (CH); Heinz Hartig, Munich (DE)

( * ) Notice: Subject to any disclaimer, the term of this patent is extended or adjusted under 35 U.S.C. 154(b) by 1503 days.

(21) Appl. No.: 11/628,375

(22) PCT Filed: Apr. 11, 2005

(86) PCT No.: PCT/EP2005/003776
§ 371 (c)(1),
(2), (4) Date: Dec. 1, 2006

(87) PCT Pub. No.: WO2005/100256
PCT Pub. Date: Oct. 27, 2005

(65) Prior Publication Data
US 2007/0181509 A1    Aug. 9, 2007

(30) Foreign Application Priority Data

Apr. 13, 2004  (EP) .................................... 04008805

(51) Int. Cl.
*C02F 1/32*    (2006.01)
(52) U.S. Cl. ..... 422/24; 422/186; 422/186.3; 210/748.1
(58) Field of Classification Search ............ 210/748.11, 210/748.01, 167.3, 198.1; 422/22, 186.3, 422/24, 186; 250/438
See application file for complete search history.

(56) References Cited

U.S. PATENT DOCUMENTS

| 3,519,817 | A |   | 7/1970 | Brunner |
| 3,767,918 | A | * | 10/1973 | Graybeal ...................... 250/433 |
| 4,968,437 | A |   | 11/1990 | Noll et al. |
| 5,393,419 | A | * | 2/1995 | Tiede et al. .................... 210/192 |
| 5,597,482 | A |   | 1/1997 | Melyon |
| 5,675,153 | A | * | 10/1997 | Snowball ....................... 250/438 |
| 5,707,594 | A | * | 1/1998 | Austin ........................ 422/186.3 |
| 5,785,845 | A | * | 7/1998 | Colaiano ..................... 210/167.3 |
| 5,961,920 | A | * | 10/1999 | Soremark ........................ 422/24 |
| 6,099,799 | A | * | 8/2000 | Anderson ................ 210/748.11 |
| 6,589,490 | B1 | * | 7/2003 | Parra .......................... 422/186.3 |
| 2004/0045886 | A1 | * | 3/2004 | Abe et al. .................... 210/198.1 |

FOREIGN PATENT DOCUMENTS

| DE | 3924349 A1 | * | 1/1991 |
| DE | 42 33 566 A1 |   | 9/1992 |
| EP | 0 470 518 A1 |   | 8/1991 |
| WO | WO 89/02418 |   | 3/1989 |
| WO | WO 95/13853 |   | 5/1995 |

* cited by examiner

*Primary Examiner* — Nam Nguyen
*Assistant Examiner* — Cameron J Allen
(74) *Attorney, Agent, or Firm* — Karl F. Milde, Jr.; Eckart Seamans; Cherin & Mellott, LLC

(57) ABSTRACT

A device for the treatment of a liquid or gaseous medium, in particular water or air, using UV radiation, comprises a UV radiation source (24), with an axial longitudinal direction and an essentially perpendicular, in particular radial direction of irradiation (R), with several layers of transmissive treatment chambers (K1-K4), serially arranged one on the other in the radiation direction (R), separated from the UV radiation source (24) and from each other by a transparent, UV-transmissive separating layer (T1-T4) which is UV transparent. The chambers, beginning with a first treatment chamber (K1), adjacent to the UV radiation source, form a flow channel for the medium running in the longitudinal direction of the UV radiation source (24), the flow channel emptying (26) into the subsequent treatment chamber (K2, K3, K4) that is at a greater distance from the UV radiation source (24) in the direction of irradiation (R).

36 Claims, 8 Drawing Sheets

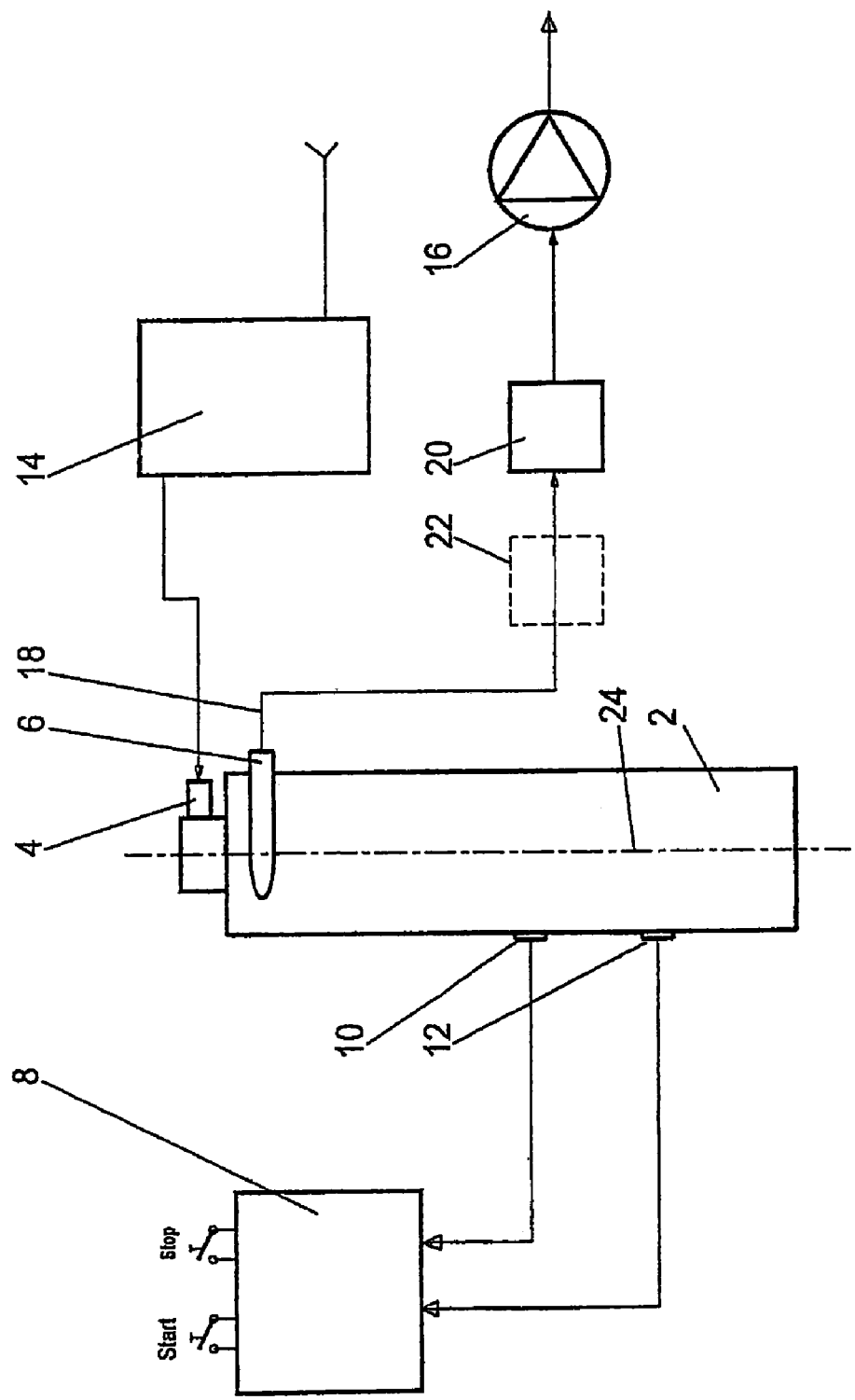

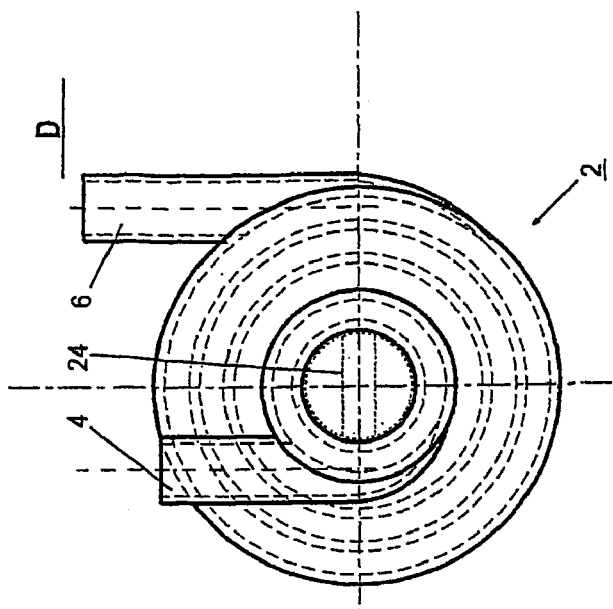
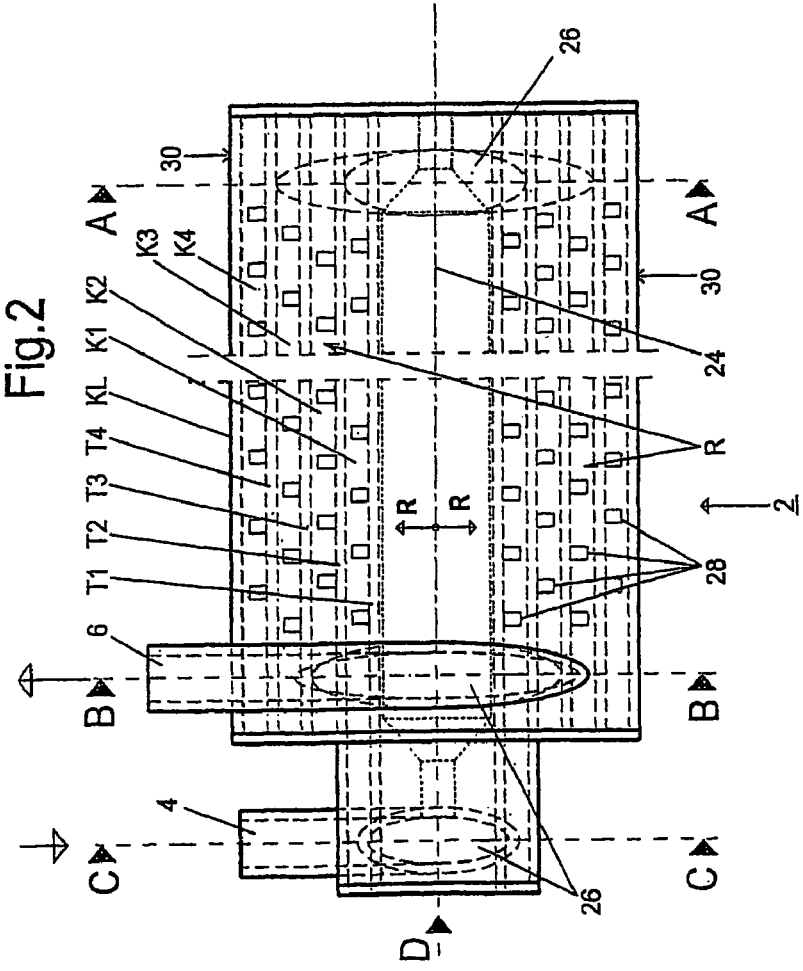

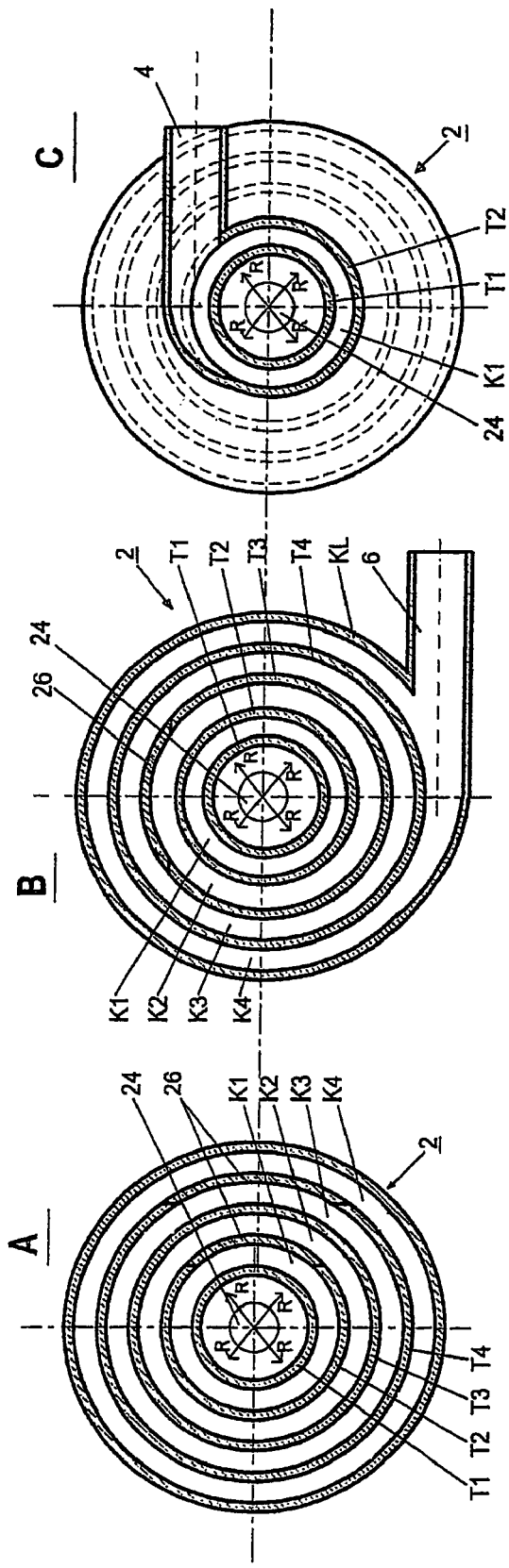

DEVICE FOR THE TREATMENT OF A LIQUID OR GASEOUS MEDIUM BY MEANS OF UV RADIATION

TECHNICAL FIELD

The present invention relates to a device for the treatment of a liquid or gaseous medium using ultraviolet radiation (UV radiation). In addition, the invention relates to a particularly suitable application of this device.

STATE OF THE ART

The term UV radiation is given to electromagnetic radiation that is located between the visible border of short-wave light and x-radiation, and that covers a wavelength range of between about 100 nm to 400 nm. A distinction is made between the following zones: UVA radiation: 400-315 nm; UVB radiation 315-280 nm; UVC radiation about 280-200 nm; VUV radiation: about <180 nm. Devices for treating liquid or gaseous mediums using UV radiation are used, for example, for UV sterilization or UV oxidation.

As a rule, UVC radiation is used for UV sterilization, which effectively destroys microorganisms such as bacteria, yeast and fungi by damaging their DNA (deoxyribonucleic acid). A UV radiation wavelength in a range of about 260 nm to 280 nm, in particular at about 254 nm, an especially high degree of sterilization results because the absorption spectrum of DNA has its maximum at about 254 nm. The high absorption of the DNA in this UV radiation range triggers a photochemical reaction, which causes a disruption of the genetic information for cell multiplication and metabolism in the irradiated microorganisms. The microorganisms are thus rendered inactive and innocuous. With UV sterilization, no addition of chemicals is necessary.

For wavelengths under 230 nm, the energy of the UV radiation is sufficient to break open chemical bonds. UV radiation with wavelengths below 200 nm include ionizing rays that trigger photochemical oxidation processes, which can be used for the purification of gases or liquids such as waste water that are contaminated with harmful substances such as pesticides, hormones, dioxin, drug residue, etc. With this UV oxidation, the molecules of the organic substances are oxidized and broken down to non-toxic compositions. This method is also referred to as photochemical wet oxidation. For industrial applications, a separate oxidizing agent (e.g., $H_2O_2$, ozone) is added to the wastewater. The UV radiation mineralizes the oxidizable substances in the wastewater. In addition, the oxidizing agent is split into highly reactive radicals. These radicals also contribute to the full oxidation of the unwanted substances in the wastewater.

Known from EP 0 470 518 A1 is a device designed as a photochemical continuous flow reactor for treating a liquid or gaseous medium using UV radiation. The preferred operation of this device used for UV oxidation is in combination with an added oxidizing agent. The device comprises a UV radiation source with an axial longitudinal direction and an essentially perpendicular direction of irradiation. In addition, the device features a treatment chamber in the form of a long stainless steel vessel that also houses the UV radiation source. The interior wall of the stainless steel vessel is polished and serves as a reflector for the UV radiation. Turbulence-inducing elements are located on the interior wall of the stainless steel vessel that mix the flowing medium and guide it into the effective zone of the UV radiation source.

To achieve a sufficient degree of sterilization or oxidation and to achieve a sufficient throughput, conventional devices for the treatment of a liquid or gaseous medium using UV radiation must exhibit a large overall size. This overall size not only requires substantial space, it also limits the operating pressure of the device significantly due to manufacturing difficulties. Furthermore, the known device requires very high energy of the UV radiation source. Additionally, it has become apparent that often a portion of the microorganisms did not become fully deactivated with conventional devices used for UV sterilization. In addition, it should be noted that even with full deactivation of the microorganisms through the destruction of their DNA, the cell shells of the microorganisms and their compositions remain largely intact. This may be harmful to persons who have a low tolerance against certain proteins or chemical compositions. In the case of incomplete UV oxidation, harmful organic substances may remain in the medium, which is also not desirable. In addition, it would be advantageous for the UV oxidation to do largely without the addition of oxidizing agents.

SUMMARY OF THE INVENTION

It is the objective, or the technical challenge, of the invention to create a simple and effective device for treating a liquid or gaseous medium using UV radiation, which essentially avoids the disadvantages inherent in the state-of-the-art. According to an additional aspect of this objective, a particularly suitable application of such a devices shall be disclosed.

According to the first aspect, this objective, as well as additional objectives which will become apparent from the discussion that follows, are achieved, according to the present invention, by providing a device for treating a liquid or gaseous medium, in particular water or air, using UV radiation which comprises: a UV radiation source with an axial longitudinal direction and an essentially perpendicular, in particular, radial direction of irradiation; several (i.e., at least two) layers of transmissive treatment chambers, serially arranged one on top of the other in the radiation direction, where said treatment chambers are each separated from the other by a transparent, UV-transmissive separating layer, and that form a flow channel for the medium beginning with a first treatment chamber that is adjacent to the UV radiation source in the direction of the irradiation running in the longitudinal direction of the UV radiation source and emptying into the subsequent treatment chamber that is at a greater distance from the UV radiation source in the direction of irradiation.

The device according to the invention operates in a continuous flow process. Preferably the UV radiation source emits UV radiation in the UVC and/or VUV range. The UV radiation source can consist of one or several individual UV radiation sources that may be located at one common location or at different locations of the device. If several individual UV radiation sources are used, it is possible that they have the same or different UV radiation spectra. For example, one individual UV radiation source may emit radiation in the UVC range and the other in the VUV range. Dependent on the respective application, the UV radiation sources may be low-pressure, medium-pressure or high-pressure emitters. The number of layers of treatment chambers can vary, in particular in correlation to the UV radiation source, the medium to be treated and its contamination. In addition, the dimensions and shapes of the respective treatment chambers, in particular their widths in the direction of radiation or their flow cross-section, respectively, may be the same or may vary. As a result, a desired flow dynamic as well as optimum utilization of the penetration depth of the UV radiation or of a particular spectral range into the medium and a certain absorption and reaction behavior can be achieved based on the respective medium to be treated. Likewise, the transparent, UV-transmissive separating layers or partial areas can exhibit the same or different properties, in particular UV transmission properties and dimensions or widths.

In comparison to conventional devices of the same genre, the device according to the invention can be designed relatively small, compact and with a low design, and requires little space. Yet it is very robust. The compact design also allows operation at a higher pressure than is possible with the state-of-the-art device; this increases the throughput of the medium or allows for the same medium throughput for smaller than the larger known devices. While known devices operate, for example, at about 1.5 bar, the device subject to the invention can easily operate at 4.5 bar, for example. Due to the layered, or multi-layered arrangement of the treatment chambers, the time of exposure of the medium to be treated, and of the contamination contained in it, can be increased significantly in the area of exposure in spite of the small design. Due to the design subject to the invention, the radiation area of the UV radiation source can be utilized optimally and the exposure time can be maximized in a small space because the medium to be treated is guided through the area of exposure of the UV radiation source several times during its travel through the device. Furthermore, because of its special design, the device subject to the invention offers addition possibilities for prolonging the time of exposure as will be described in greater detail below.

Because of the increased exposure time of the medium to be treated in the irradiation area of the UV radiation source, the device subject to the invention has a significantly improved degree of sterilization or oxidation compared to the known solutions. Microorganisms contained in the medium can be deactivated reliably. And potential harmful organic substances can be fully oxidized or broken down to non-toxic compositions. Furthermore, a particular advantage of the device according to the invention is that it can be used to carry out a combined UV sterilization and UV oxidation process (following called combined UV process for short) within one single unit. This possibility is primarily the result of the special layered arrangement of the successive treatment chambers transmissive to UV radiation combined with the increased exposure time of the medium and the duration that the UV radiation can act on the medium and its contamination. With a suitable selection of the UV radiation source's spectral range, the combined UV process both sterilizes the medium by damaging the DNA of the contained microorganisms and destroys and fully breaks down the molecular composition of the remaining deactivated microorganisms or viruses through photochemical oxidation (e.g., in the course of a wet oxidation). The result is a very high degree of purification.

Potential effects from low tolerances against certain proteins or chemical compositions of deactivated but physically still present microorganisms or microorganism residue in the medium that may occur with conventional UV sterilization are avoided. Depending on the type of radiation source used, or the arrangement of the individual UV radiation sources, with this achievable combined UV process, the UV sterilization and the UV oxidation can effectively transition seamlessly into each other or can be carried out sequentially in succeeding treatment chambers.

Thus, the device according to the invention enables the carrying out of a process that corresponds to a natural process attainable through the UV radiation of the sun, where in the end non-toxic and no longer active substances or compositions remain, which in turn can be returned to the biological cycle.

Although in principle it is possible to use separate oxidizing agents during the UV oxidation with the combined UV process that can be realized with the device according to the invention, as a rule this is not necessary because of the achievable high efficiency. Thus, the risks associated with the use of such chemicals can be avoided. Due to the optimum utilization of the UV radiation, the device subject to the invention requires only one UV radiation source with a comparatively low energy. Thus, the device according to the invention operates with high efficiency, low operating costs, low maintenance expenses and, therefore, great cost-effectiveness.

According to a second aspect of the invention, the principal objective underlying the invention is achieved through the application of the device as described above for the combined UV sterilization and UV oxidation (called combined UV process above), in particular for water treatment.

Essentially, the same advantages presented prior in connection with the device subject to the invention can be attained with the application subject to the invention.

Preferred exemplary embodiments of the invention with additional design details and additional advantages are described and explained in greater detail below with reference being made to the attached drawings.

BRIEF DESCRIPTION OF THE DRAWINGS

FIG. 1 is a schematic block diagram of a first embodiment of a device according to the invention.

FIG. 2 is a schematic view of a longitudinal section through an essential component of the device according to the first embodiment of the invention.

FIG. 3 is a schematic view of a cross-section along the line A-A in FIG. 2.

FIG. 4 is a schematic view of a cross-section along the line B-B in FIG. 2.

FIG. 5 is a schematic view of a cross-section along the line C-C in FIG. 2.

FIG. 6 is a schematic top view of the device of FIG. 2 in the direction shown by the arrow D in FIG. 1.

DESCRIPTION OF THE PREFERRED EXEMPLARY EMBODIMENTS

Figure 7:
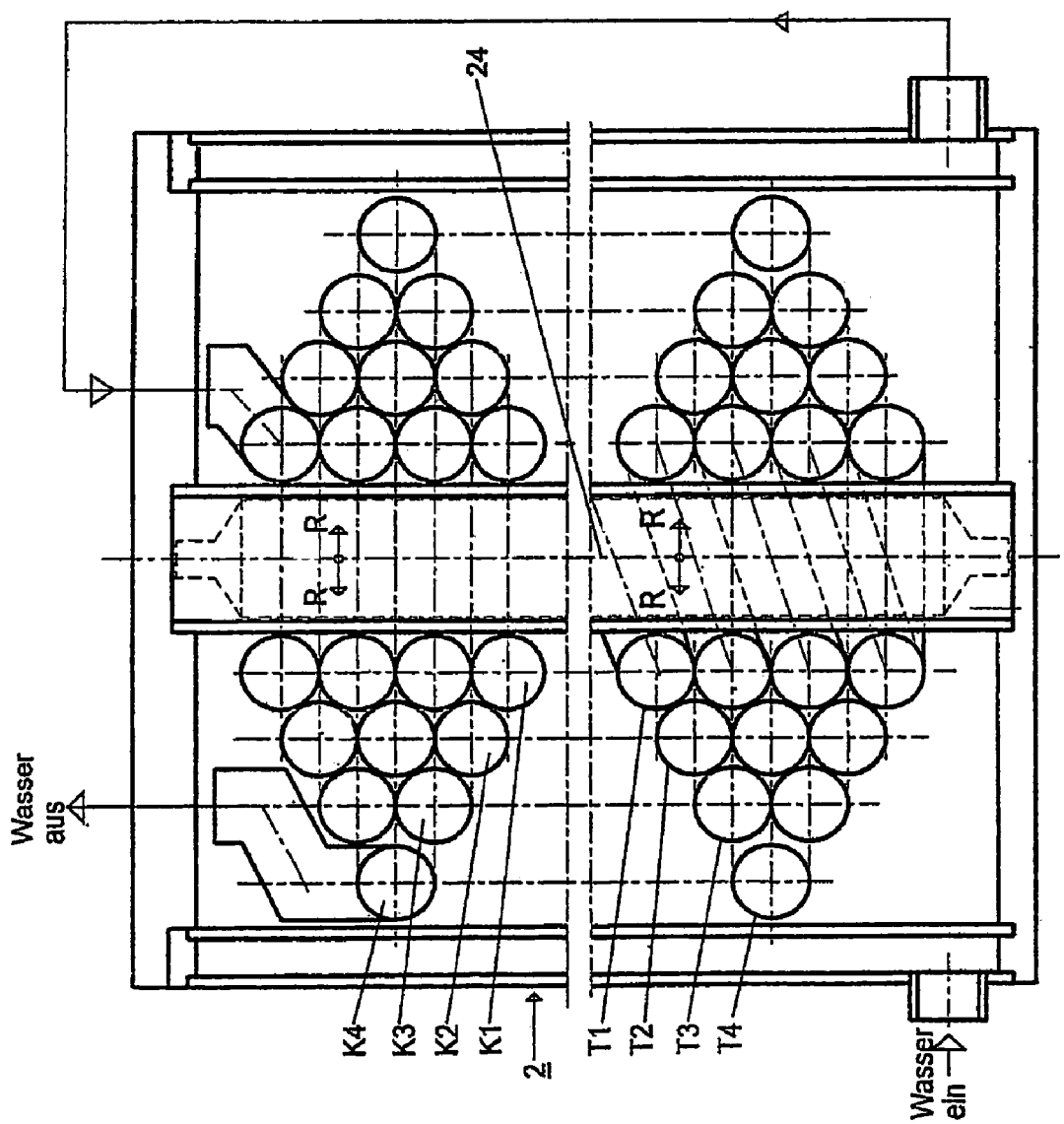
FIG. 7 is a schematic view of a longitudinal section through a second embodiment of a device according to the invention.

To avoid repetition in the subsequent description and in the figures, the same parts and components are designated with the same reference characters as long as further differentiation is not necessary or not useful.

FIG. 1 shows a schematic block diagram of a device according to the invention for treating a liquid or gaseous medium using UV radiation according to a first embodiment. As essential components, the device comprises a reactor 2 with a supply channel 4 for the liquid or gaseous medium to be treated and an outlet channel 6 for the treated medium. In the exemplary embodiment at hand, water that is contaminated with microorganisms or viruses as well as harmful organic substances is used as the medium to be treated.

The reactor 2 is coupled with a control device 8, which in this case features two safety and control sensors 10, 12 (here: one optical sensor and one temperature sensor). In addition, the device exhibits a pre-filter device 14 upstream of the supply channel 4 as well as a pump 16, which is located in a line 18 that is connected to the outlet channel 6. A solenoid valve 20 is provided between the outlet channel 6 and the pump 16. A filter device 22 (e.g., an activated carbon filter) may also be provided in the line 18 downstream from the outlet channel 6 for purposes of filtering out potential radical residue and/or residual ozone from the treated medium.

FIG. 2 shows a schematic view of a longitudinal section through the photochemical continuous flow reactor 2 of the device subject to the invention according to the first embodiment. FIG. 3 shows a schematic view of a cross-section along the line A-A in FIG. 2. The device, or the reactor 2, respectively, comprises a UV radiation source 24 with an axial longitudinal direction and an essentially perpendicular, in particular, radial direction of irradiation R. The UV radiation source 24 features a UV radiation spectrum with a wavelength from at least 180 nm to at least 254 nm. In this present case, the UV radiation spectrum is in a range from about 180 nm to about 260 nm.

In addition, the device exhibits several layers of transmissive treatment chambers (K1 to K4), serially arranged or layered one on top of the other in the direction of irradiation. The treatment chambers K1-K4 each are separated from the UV radiation source 24 and from the other by a transparent UV transmissive separating layer T1 to T4. Beginning with a first treatment chamber K1 that is adjacent to the UV radiation source 24 in the direction of the irradiation R, the treatment chambers K1-K4 form a flow channel for the medium running in the longitudinal direction of the UV radiation source 24 and emptying into the subsequent treatment chamber that is at a greater distance from the UV radiation source 24 in the direction of irradiation R.

As indicated in FIGS. 2 and 3, in the shown example the reactor 2 has four treatment chambers K1, K2, K3, K4, and their lengths correspond essentially to the axial length of the UV radiation source 24. In the radial direction, the treatment chambers K1-K4 are arranged concentrically around the UV radiation source 24. Each treatment chamber K1-K4 exhibits a circular cross-section. The treatment chambers K5-K5 are separated from each other by five separating layers. At least the first four separating layers T1-T4 are transparent to the UV radiation.

With the first embodiment, beginning at the UV radiation source 24 in the direction of irradiation R, both the first separating layer T1, which is located between the UV radiation source 24 and the first treatment chamber K1 and which is closest to the UV radiation source 24 and the, in radial direction next, second separating layer T2 are made of a first separating layer material. This first separating layer material exhibits a UV transmittance that is essentially transmissive to the entire UV radiation spectrum of the UV radiation source 24, including a first partial spectrum with wavelengths below 200 nm, i.e., the UV radiation at about 180 nm. The first two separating layers T1, T2 are designed in the shape of glass tubes that are made of synthetic quartz glass as the first separating layer material.

Fundamentally, the first separating layer T1, or the first glass tube, respectively, could also be a transparent sleeve wall of the first UV radiation source 24 itself that is transmissive to the aforementioned spectral range. This appears prudent, for example, if a submersible UV lamp that is located in the first treatment chamber K1 is used as the UV radiation source 24.

The overall thickness, measured in the direction of irradiation R, of the partial layer formed by the first two glass tubes T1, T2 and the first two treatment chambers K1, K2, into which the UV radiation enters through the synthetic quartz glass is selected such that it essentially corresponds to a maximum effective penetration depth of the first partial spectrum of the UV radiation, said penetration depth being a factor of the absorbability of the water to be treated and the UV transmittance of the first two glass tubes T1, T2 for this first partial spectrum. This allows for an optimum utilization of the short-wave, hard UV radiation below 200 nm for the purpose of generating ozone or radicals as will be described below. A greater layer thickness is not useful, on the contrary, it may be hazardous because some areas of the water to be treated will not be penetrated reliably or cannot be covered.

The separating layers that are viewed radially further toward the outside, i.e., here at least the third and fourth separating layer T3, T4 that follow in the direction of irradiation R after the first and second separating layer T1, T2, are made of a second separating layer material. This second separating layer material exhibits a UV transmittance that allows only UV radiation in a second partial spectrum of the UV radiation source 24 with wavelengths greater than 200 nm to pass through. The third and fourth separating layers T3, T4 are also formed in the shape of glass tubes made of natural quartz glass as the second separating layer material.

In addition, the device subject to the invention features an exposure time prolongation device for prolonging the exposure time of the water to be treated and of the contamination or harmful substances contained in it in the radiation zone of the UV radiation source 24. The successive treatment chambers K1-K4 form a part of the exposure time prolongation device. This is the case because during the operation of the device, the water flows first through the supply channel 4 into the first, radially inner, chamber K1, in it in the longitudinal, axial direction of the UV radiation source 24 to an outlet opening at the end, which at the same time forms the inlet opening 26 for the next, i.e., the second radially subsequent treatment chamber K2. The water is redirected about 180°, flows again along the longitudinal direction of the UV radiation source 24 and enters into the third treatment chamber K3 which is radially further outside, where it is again redirected by 180°. From the third treatment chamber K3 it flows in a similar manner into the fourth, radially outermost chamber K4 and exits the device through the outlet channel 6. The water is exposed to the UV radiation along its entire flow path through the treatment chambers K1-K4.

The exposure time prolongation device comprises still additional elements, which are described below with reference to FIGS. 4 to 6. FIG. 4 shows a schematic view of a cross-section along the line B-B in FIG. 2; FIG. 5 shows a schematic view of a cross-section along the line C-C in FIG. 2; FIG. 6 shows a schematic top view of the device of FIG. 2 with a directional view according to the arrow D in FIG. 1.

As indicated in FIG. 4, the supply channel 4 is designed as part of the exposure time prolongation device such that it empties tangential into the first treatment chamber K1 with regard to the radial direction of irradiation R, or the ring-shaped cross-sectional shape of the first treatment chamber K1. This gives the supplied water a rotation such that it flows in the first treatment chamber K1 in an almost helical path around the UV radiation source 24 from the supply opening 4 to the outlet opening 26 of the first treatment chamber K1. The outlet opening 26 of the first treatment chamber K1 or the supply opening 26 of the second treatment chamber K2 is designed slot-shaped, for example, with a lens-like slot cross-section (cf. FIGS. 2 and 3), such that the water can flow into the second treatment chamber K2 in the direction of its rotation essentially without restrictions. This process is supported by the centrifugal forces caused by the rotational movement. The subsequent outlet or supply openings 26 of the respective succeeding treatment chambers K3, K4 are designed accordingly.

The outlet channel 6 is designed as a part of the exposure time prolongation device as well. Relative to the radial direction of irradiation R or the circular cross-sectional shape of the treatment chambers K1-K4, respectively, it exists essentially tangentially and in the direction of the rotation from the last treatment chamber K4, which has the furthest distance from the UV radiation source 24 in the direction of the radiation R, and contributes in this manner to the maintenance of the helical flow around the radiation source 24.

In addition, the exposure time prolongation device can exhibit turbulence elements 28 or turbulators, which may be located in the treatment chambers K1-K4, the supply channel 4, the outlet channel 6, the supply or outlet openings 26 between successive treatment chambers or additional supply and outlet lines. Nap-like elevations, indentations, vanes, wings, fences, rotating or pivoting components or the like on the walls of said components may serve as the turbulence elements 28. If these turbulence elements 28 are to be used in connection with said tangential supply channel 4 and outlet channel 6, they should contribute to the maintenance of the fundamental rotational direction. The turbulence elements 28 can be installed permanently or located on removable inserts, which simplifies cleaning. In FIG. 2, turbulence naps that are located at the glass tubes T1-T4 are indicated.

The last, i.e., the fourth treatment chamber K4 features at the side that is furthest away from the UV radiation source 24 in the radiation direction, a reflection device 30, which reflects back the UV radiation that has been emitted by the UV radiation source 24 and has penetrated to the outer wall KL, contributing in this manner to a high degree of utilization of the UV radiation and to an intensive treatment of water. If the outer wall KL of the last treatment chamber K4 is non-transmissive for the UV light, the UV reflection device 30 may be a mirror coating applied to the inside of this wall KL, or a well polished reflecting surface. However, if the outer wall KL is transmissive to UV radiation (e.g., made of natural quartz glass) then the UV reflection device 30 may be designed as reflection or mirror coating or the like applied around the glass.

Following is a description of the device according to the invention.

The control device 8 is used to start the operation of the device and the UV radiation source is activated. After a specified burn-in time, the solenoid valve 20 is opened and the pump is actuated. Contaminated water is drawn through the pre-filter device 14 into the reactor 2 and through its treatment chambers K1-K4, where it is sterilized and freed of chemical contamination, and then exits via the outlet channel 6, potential post-filters, the solenoid valve and the pump 16. During operation, it is the task of the optical sensor 10 to sense a haze on the glass walls of the glass tubes T1-T4. Such a haze may be caused by calcium deposits and/or turbid water, for example. It would reduce the performance of the reactor. At a defined degree of haze, a sensor signal alerts the control device 8 of this condition. If the haze exceeds a specified threshold, the control device 8 shuts down the UV radiation source 24, the solenoid valve 20 and the pump 16, and prevents the unit from restarting. Operation is permitted only after cleaning or error correction.

The task of the temperature sensor 12 is to protect the reactor from overheating. For example if the water flow were obstructed, the reactor would heat up and might even bring the water in the reactor to a boil. The sensor 12 signals such a hazardous condition to the control device 8, which then shuts down the UV radiation source 24, the solenoid valve 20 and the pump 16.

In the device according to the invention, the cleaning process is carried out in the following manner:

The polluted water, contaminated with microorganisms or viruses, is exposed to UV radiation in the first and second treatment chambers K1, K2 at a UV radiation spectrum of both below and above 200 nm. The UV radiation above 200 nm, in particular at about 254 nm, causes the UV sterilization by destroying the DNA of the microorganisms contained in the water. The radiation underneath 200 nm, in particular at about 180 nm, initiates the UV oxidation in the course of a photochemical wet oxidation.

The radiation below 200 nm produces ozone ($O_3$) from the molecular oxygen ($O_2$) contained in the water. This occurs in the first and second chamber. The present UV radiation above 200 nm breaks down the ozone into individual (single) oxygen atoms (O). These already highly reactive oxygen atoms combine with hydrogen atoms (H+) to OH molecules as a result of the photochemical reaction. OH molecules are free radicals, which essentially destroy all the types of harmful organic substances described above, especially the molecular remnants or shells of the deactivated microorganisms. OH radicals have a max. lifespan of about 100 milliseconds. Thereafter, they disintegrate into hydrogen and oxygen, i.e., into entirely nontoxic substances. With a photochemical reaction, no harmful substances remain. All organic substances are fully oxidized. Even substances such as plant protectants (DDT, Atrazine, etc.) or interim products of chemical reactions are oxidized into nontoxic residue.

With the device subject to the invention, the generation of radicals occurs in the first two treatment chambers K1, K2. Since the water containing the radical flows continuously, the oxidation ("the consumption") of the radicals occurs mainly in the third and fourth treatment chamber K3, K4. The inherent or added exposure time prolongation device of the device subject to the invention described above allows for the generation of a high radical density and at the same time increases the target reliability of the OH radicals on the molecular structure to be destroyed through the generated water turbulence. The exposure times necessary for the photochemical wet oxidation is more than fulfilled with the design subject to the invention. For example, the required exposure time for oxidizing proteins is about 100 ms. The max. exposure time obtainable at a flow rate of, for example, 3.8 l/min in the reactor of the device subject to the invention is about 6000-7000 ms.

Since the third and fourth glass tube T3, T4 are made of normal or natural quartz glass and UV radiation below 200 nm is not transmitted, and in addition the UV radiation below 200 n=essentially had already been fully absorbed in the first and second treatment chambers K1, K2, it is no longer effective in the third and fourth treatment chambers K3, K4. Thus, for the third and fourth treatment chambers K3, K4, separating layers T3, T4 made of normal or natural quartz, which is transmissive to UV radiation above 200 nm, are entirely sufficient. The water exits the last treatment chamber K4 tangentially, and it is then available sterilized and free of harmful organic substances and residues of microorganisms or viruses.

Thus, a combined UV sterilization and UV oxidation (called combined UV process above) occurs continuously in the device subject to the invention ensuring a very high degree of purification of the contaminated water.

After the treatment in the reactor 2, the sterilized and purified water should be guided across an activated carbon filter for safety purposes, which can be done in the post filtration device 22. Activate carbon restores a natural redox value. Due to the OH radicals, an enormously high redox potential of up to 2 Volt exists in the treatment chambers K1-K4 of the reactor 2. This is harmful and must be restored to natural conditions (250-450 mV).

FIG. 7 shows a schematic view of a longitudinal section through a device subject to the invention according to a second embodiment. With this variation, the respective layered treatment chambers K1-K4 are arranged helically around the UV radiation source 24.

Figure 8:
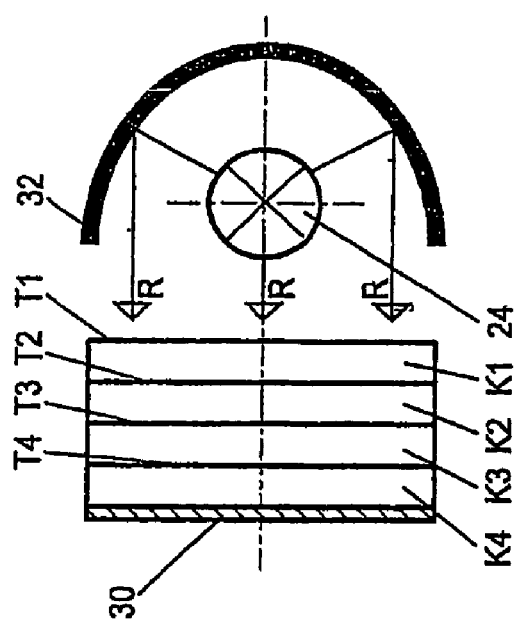
FIG. 8 is a schematic view of a cross-section through a third embodiment of a device according to the invention.

FIG. 8 shows a schematic view of a cross-section through a device subject to the invention according to a third embodiment. The functional principle of this variation corresponds essentially to that of the first embodiment, however the layered treatment chambers K1-K4 are grouped in a plate- or box-like arrangement and the UV radiation source 24 is placed on the side of this arrangement. Each treatment chamber K1-K4 exhibits a meander-like flow path (not shown) for the medium to be treated. For a greater yield of the UV light, the device is equipped with a parabolic reflection device 32, which focuses the UV light emitted by the UV radiation source 24 onto the layered treatment chambers K1-K4.

Figure 9:
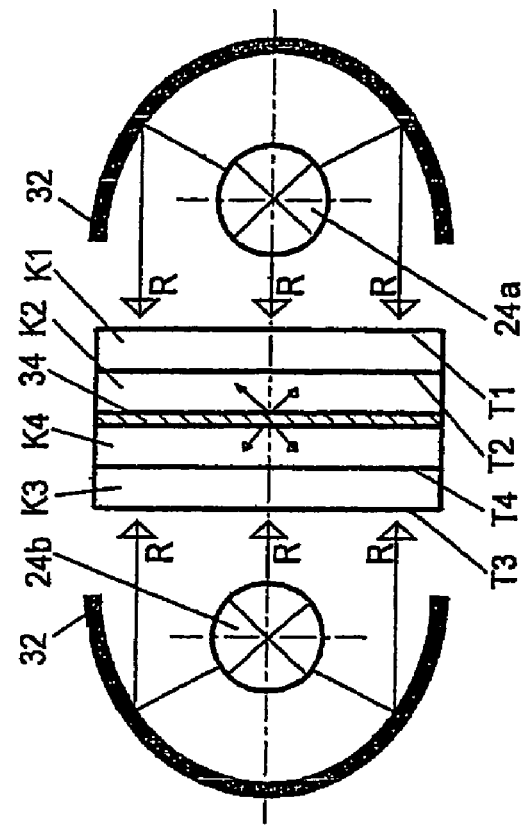
FIG. 9 is a schematic view of a cross-section through a fourth embodiment of a device according to the invention.

FIG. 9 shows a schematic view of a cross-section through a device subject to the invention according to a fourth embodiment. The embodiment according to FIG. 9 is in principle similar to that according to FIG. 8, however, two individual UV radiation sources 24a, 24b are provided that irradiate the layered treatment chambers K1-K4 from two different sides. The first individual UV radiation source 24a emits UV light at a spectrum below 200 nm and the second 24b at a spectrum above 200 nm. If a group of treatment chambers is assigned to each of these individual UV radiation sources 24a, 24b, and if, for example, a filter or a separating UV reflection device 34 is located between them, then the UV sterilization and the UV oxidation can occur separated by time and location within the device, for example, the UV sterilization first followed by the UV oxidation. The first or second material for the respective transparent, UV-transmissive separating layers can act as the filters.

Figure 10:
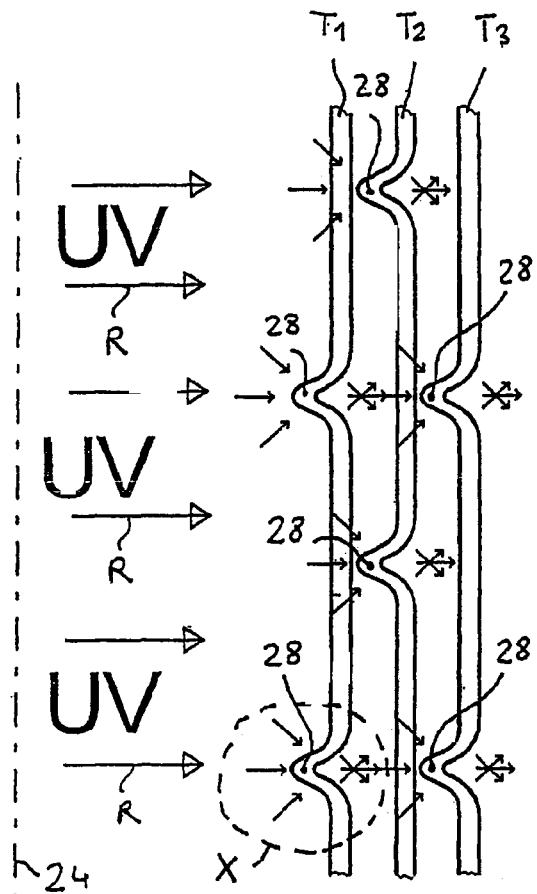
FIG. 10 is a schematic view of a longitudinal section through an essential area of a fifth embodiment of a device according to the invention.

FIG. 10 shows a schematic view of a longitudinal section through an essential area of a device subject to the invention according to a fifth embodiment. With this variation, the turbulence elements 28 or turbulence naps of the exposure time prolongation device are designed transparent and UV-transmissive. The transparent and UV-transmissive turbulence elements 28 are at the same time an integral part of a respective transparent, UV-transmissive separating layer T1, T2, T3.

More precisely, in this example, three-dimensionally formed areas of the respective separating layer T1, T2, T3 form the transparent and UV-transmissive turbulence elements 28. They may be manufactured, for example, during the manufacturing process of the glass tubes that form the separating layers T1, T2, T3 by plastic deformation of the glass tubes under heat. It is also possible to use separate, i.e., designed as independent individual parts, transparent and UV-transmissive turbulence elements 28, that are attached at or on the respective transparent, UV-transmissive separating layer T1, T2, T3.

In the presented case, the transparent, UV-transmissive turbulence elements 28 are designed as optical lenses (e.g., condensing lenses or dispersing lenses) and/or as light conductors with precisely defined optical properties. They have, therefore, a dual function because they affect turbulence in the medium to be treated and in the process increase its exposure time to the UV radiation but they also focus (or disperse) the UV beams in a clearly defined manner and can thus attain a greater yield of the UV radiation. For this reason, they will be called opto-mechanical naps 28 from here forward. When viewed in the direction of the irradiation R, the opto-mechanical naps 28 exhibit an essentially circular layout. Depending on the embodiment, they may also have an oval, square, rectangular or polygonal shape or have an irregular or asymmetrical layout.

As can be recognized in FIG. 10, the protrusions of the opto-mechanical naps 28 of the respective separating layers T1, T2, T3 curve in this example in the opposite direction to the direction of irradiation R of the UV beams. In other words, they are located on the side of the respective separating layer T1, T2, T3 that is directed toward the UV radiation. Depending on the lens type that is formed by an opto-mechanical nap, the opto-mechanical naps 28 may also be located on the side that is directed away from the UV radiation or even on both sides. The rear sides of the naps 28 form indentations, which serve as turbulence elements like the protrusion on the front side. As is also clearly apparent from FIG. 10, the naps 28 of a first separating layer (e.g., T1) are offset versus the naps of a second separating layer (e.g., T2).

The nap height or the distance of the nap tips, respectively, is selected in relation to the width of a treatment chamber defined by the respective separating layers T1, T2, T3 measured in the direction of irradiation R such that the height or the distance, respectively, exhibits a specified value. Expressed more precisely, the distance from an optical inlet plane (or outlet plane) of an opto-mechanical nap 28 of a separating layer (e.g., T2) that is located distal from the UV radiation source in the direction of irradiation R is located proximal at a distance from the optical outlet plane (or inlet plane) of a separating layer (e.g., T1) in the direction of the irradiation R from the UV radiation source, which is preferably less than or equal to 15 mm, in particular less than or equal to 10 mm (depending on the design also less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, less than or equal to 1 mm, less than or equal to 0.5 mm, less than or equal to 0.25 mm). For example, the nap tip, or the nap head of an opto-mechanical nap 28 of the separating layer T2 in this example is at a distance of about 0.5 mm from the side of the separating layer T1 that is on the side that is directed away from the UV radiation source, such that the aforementioned condition is fulfilled. Corresponding distances are preferably selected for the naps 28 of the other separating layers (here: T3 in relation to T2).

In this way, the UV radiation with a wavelength below 200 nm (here: e.g., 185 nm) need only travel a short distance of max. 10 mm between the respective optical outlet and inlet plane through the medium to be treated (e.g., water) and is not dampened too much. This short-wave UV radiation can therefore be transported through the opto-mechanical naps 28 into treatment chambers that are located at a greater distance from the UV radiation source 24, and can there be used for the photo-reaction/UV oxidation and for generating ozone or radicals, respectively.

If required, the same effect can be achieved for the longer-wave UV radiation above 200 nm (e.g., 254 nm) with a sterilizing effect using the opto-mechanical naps 28. Fundamentally, the respective distance should be selected corresponding to the respective wavelength of the partial UV spectrum to be viewed, the width of the treatment chamber that is determined by the reciprocal distance of the separating layers, and thus the distance to be bridged by the UV radiation between two adjacent separating layers, and the type of medium to be treated.

Therefore, the device subject to the invention can be equipped with a greater number of treatment chambers and can purify a greater amount of the medium to be treated than would be possible without the opto-mechanical naps 28 without increasing the energy or the energy consumption, respectively. The achievable degree of purification is dependent on the number of opto-mechanical naps 28, their optical quality and the medium to be treated.

Figure 11:
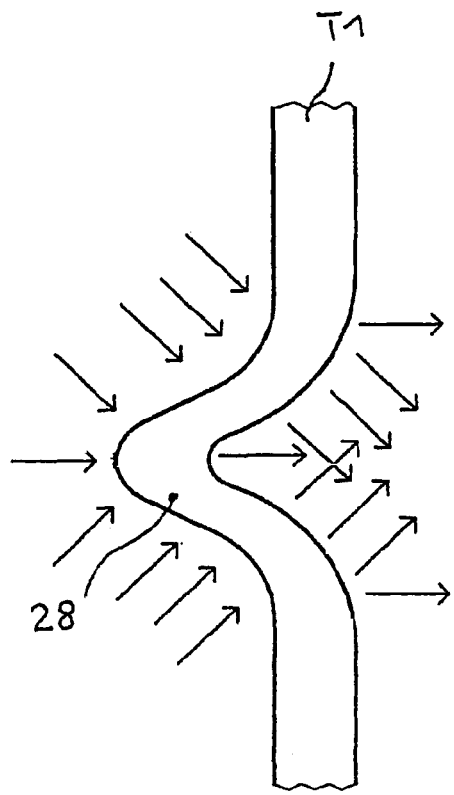
FIG. 11 shows a magnification of an area X from FIG. 10.

In FIG. 11, which shows a magnification of the area X of FIG. 10, the beam path of the UV radiation generated by an opto-mechanical nap is shown in more clarity. As can be seen, the opto-mechanical nap 28 acts essentially as a condensing lens (in the manner of a dome lens) that focuses the incoming UV radiation and passes it on in a bundled manner.

Figure 12:
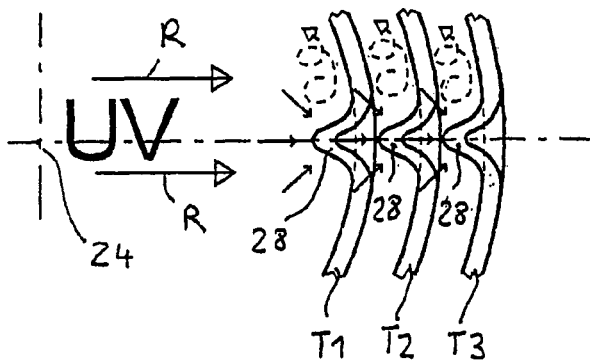
FIG. 12 is a schematic view of a cross-section through an essential area of a device subject to the invention according to a sixth embodiment.

FIG. 12 shows a schematic view of a cross-section through an essential area of a device subject to the invention according to a sixth embodiment. This variation is essentially similar to that of FIGS. 10 and 11. However, in this case the opto-mechanical naps 28 of the successive separating layers T1, T2, T3 are arranged in succession viewed in the direction of the irradiation R. A combination of the arrangement of the naps 28 in FIGS. 10, 11 and 12 is possible as well. FIG. 12 again indicates through thin, dashed lines the turbulence of the medium to be treated caused by the opto-mechanical naps 28 and resulting in an increase in the exposure time of the medium in the UV radiation.

With the device subject to the invention according to FIG. 12, the opto-mechanical naps 28 are arranged successively in the direction of irradiation R of the UV light source such that an optical outlet plane (or inlet plane) of an opto-mechanical nap 28 of a first separating layer (e.g., T1) is arranged at a distance from an optical inlet plane (or outlet plane) of an opto-mechanical nap 28 of a succeeding—viewed in the direction of the irradiation R—second separating layer (e.g., T2), where said distance is preferably less than or equal to 15 mm, in particular less than or equal to 10 mm (depending on the design also less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, less than or equal to 1 mm, less than or equal to 0.5 mm, less than or equal to 0.25 mm). In this manner, the same effects and advantages are achieved that have already been described in connection with the equivalent distances for the device according to FIG. 10.

In the embodiments according to FIGS. 10 to 12, depending on the inflection, the transparent UV-transmissive separating layers T1, T2, T3 may also affect converging or dispersing effects that can be combined with those of the opto-mechanical naps 28.

Figure 13:
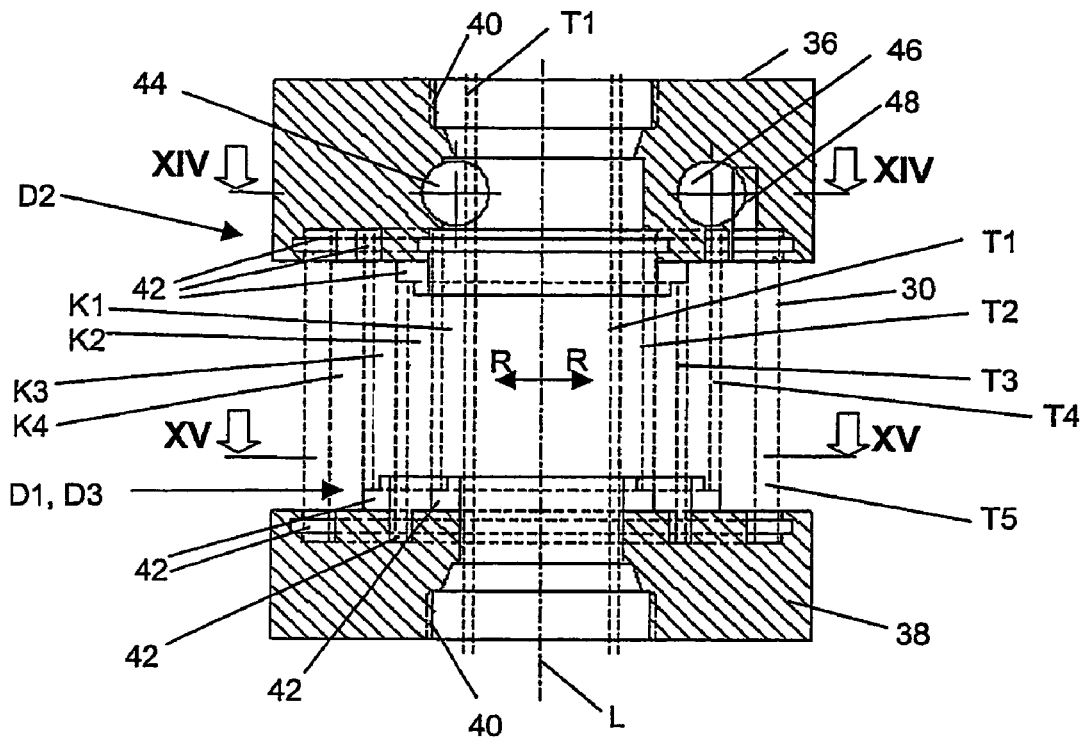
FIG. 13 shows a schematic view of a longitudinal section through a sixth embodiment of a device according to the invention.
Figure 14:
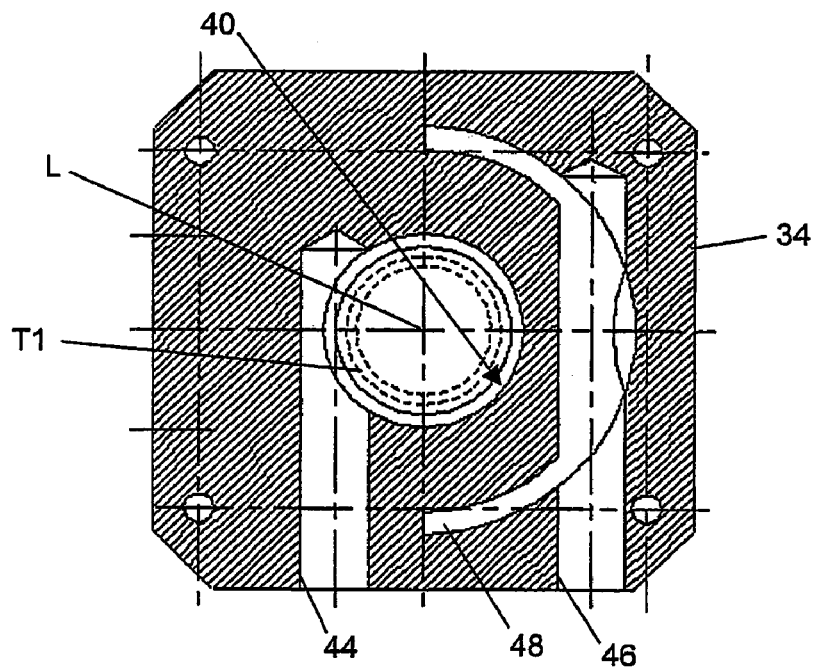
FIG. 14 is a schematic view of a cross-section along the line XIV-XIV in FIG. 13.
Figure 15:
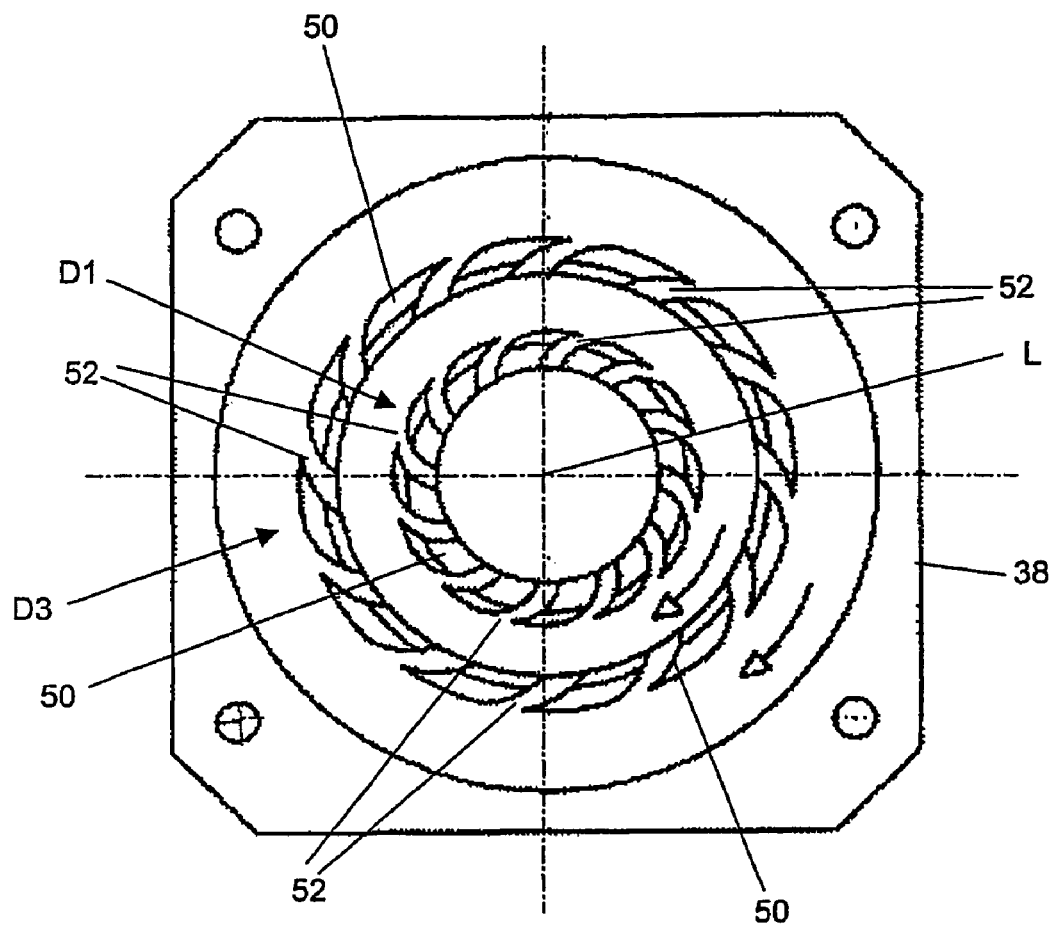
FIG. 15 is a schematic view of a cross-section along the line XV-XV in FIG. 13.

FIG. 13 shows a schematic view of a longitudinal section through a device subject to the invention according to a seventh embodiment. FIG. 14 shows a schematic view of a cross-section along the line XIV-XIV in FIG. 13. And FIG. 15 shows a schematic view of a cross-section along the line XV-XV in FIG. 13. This seventh variation corresponds in its basic principle to the embodiments explained above, however, it exhibits some special features compared to them.

For example, the device according to FIG. 13 features an upper 36 and a lower removable cover 38 with four concentric, round quartz tubes located between them and forming the UV-transmissive separating layers T1-T4, as well as an outer, round quartz glass tube T5, which forms a UV reflection device 30. At its outside, the outer quartz glass tube T5 is mirrored by vapor-deposition of an aluminum coating and reflects back the—in the direction of the direction of irradiation—incoming UV radiation that has passed through the quartz glass tube T5 and has reached the aluminum coating against the direction of the irradiation R. All the quartz glass tubes T1-T5 are sealed against the covers 36, 38 using not shown seals. This ensures easy replaceability of the respective components and especially easy assembly and disassembly of the quartz glass tubes T1-T5 as well as simplified maintenance and repair.

The innermost quartz glass tube T1 stretches across a central passage opening 40 along through the covers 36, 38 and is open or can be opened at least on one side. In this manner, the UV radiation source (not shown here for better clarity) can be mounted through the tube opening in the inside of the tube T1 and the device or removed again if need be, without requiring a disassembly of the separating layers T1-T5, or of the covers 36, 38.

The covers 36, 38 each feature a centering device 42 for the UV-transmissive separating layers T1-T5 or the tubes located between them, such that they can be easily and securely arranged at a predetermined position to each other and at the covers 36, 38. The centering device 42 comprises grooves and/or protrusions and/or recesses or the like in or on or at which the respective tubes T1-T5 can be inserted or fitted. The innermost tube T1 is centered by the passage opening 40 and its seals. Due to this design, it is not necessary to mold or glue the quartz glass tubes T1-T5 into the covers 36, 38, which additionally simplifies maintenance or repair.

As can be seen in FIGS. 13 and 14, the upper cover 36 features an inlet 44 and an outlet 46 for the medium to be treated. Basically, the inlet 44 and the outlet 46 could also be provided at the lower cover 38. It is also possible that a respective cover 36, 38 exhibits either only an inlet 44 or an outlet 46. The inlet 44 opens into the radially innermost treatment chamber K1. The outlet 46 communes with the radially outermost treatment chamber K4 via a semi-circular channel 48.

Connecting channels 50 or "passage channels" are provided in the upper cover 36 for the medium to be treated to pass from one treatment chamber to the respective next one, with said channels connecting one treatment chamber K1-K3 with the respective subsequent treatment chamber K2-K4 (ref. FIG. 15, for example). Fundamentally, the connecting channels 50 can also be located in the lower cover 38 or in both covers 36, 38.

In addition, the seventh embodiment exhibits an additional design feature in the exposure time prolongation device. I.e., alternative to or in addition to the components of the exposure time prolongation device described above, it exhibits a part that is, in this case, located in the upper 36 and the lower cover 38. Expressed more precisely, the part of the exposure time prolongation device located in the upper 36 and the lower cover 38 features a turbulence device for the medium to be treated. In this exemplary embodiment, this turbulence device is integrated into the connection channels.

The turbulence device comprises a nozzle device with numerous nozzles 50, whose nozzle channels are designed as connection channels 52 as indicated in FIG. 15 (for clarity sake, the quartz glass tubes T1-T5 are not shown in FIG. 15).

Numerous nozzles 50 are provided between each two successive treatment chambers (here: K1-K2, K2-K3, K3-K4), with said nozzles being arranged like a ring around the longitudinal axis L referenced to a longitudinal axis L of the treatment chambers (K1-K4) or of the device, respectively. The nozzles 50 of such a nozzle ring are designated as nozzle levels D1 to D3 for short. Recognizable in FIG. 15 at the lower cover 38 are a first and a second nozzle level D1 and D3. A third nozzle level (D2) is located at the upper cover 36 (FIG. 13). In this example, no nozzle level is required between the inlet 44 and the first treatment chamber K1, because the inlet 44 opens essentially tangential into the first treatment chamber K1, such that the inflowing medium rotates in the chamber K1 around the UV radiation source and continues to flow helically to the first nozzle level D1. Fundamentally, a nozzle level could also be provided at the inlet to the first treatment chamber K1.

In this example, some areas of the nozzles levels D1 to D3 also function as centering devices 42 for the quartz glass tubes T1-T4. The nozzle levels D1 to D3 are located between two successive treatment chambers alternating at the upper and at the lower cover 36, 38, such that in FIG. 15 only the two nozzle levels D1 and D3 can be recognized. The nozzle levels D1-D3 are each provided in recesses (or indents or the like) at the bottom side of the upper cover 36 and on the top side of the lower cover 38. Fundamentally, the nozzle levels can also be provided at only one cover.

The nozzles 50 are each designed such that their nozzle outlet openings that open into a respective treatment chamber K2-K4 define a predetermined output direction for the medium to be treated. This output direction is selected such that is essentially tangential or at an oblique angle in relation to the ring shape of the treatment chambers K2-K4 and to the direction of irradiation R of the UV radiation source. The output direction of the nozzles 50 may also exhibit a component that stretches in the longitudinal direction. However, it should preferably be small. These measures cause the medium that is injected into the respective treatment chamber K2-K4 to be in rotation. And the medium rotates—just as in the chamber K1—in the treatment chambers K2 to K4 in a circular or helical shape around the UV radiation source.

In this manner, the path that the medium to be treated travels inside the device is prolonged by about 480% per treatment chamber K1-K4. The medium rotates in the treatment chambers K1-K4 at a high speed around the UV radiation source until it exits the last treatment chamber K4. The medium and the potential contaminates contained in the medium are, therefore, exposed to the radiation of the UV radiation source for a longer time, which allows for an optimum utilization of the sterilization and oxidation performance.

The nozzle outlet openings and the output directions of the nozzles 50 of two successive treatment chambers K1-K2, K2-K3, K3-K4 are preferably oriented in opposite directions to each other such that the rotational direction of the medium is reversed when transitioning from one treatment chamber to the next. This too contributes to the prolongation of the exposure time of the medium to the radiation of the UV radiation source and thus promotes an improved utilization of the sterilization and oxidation performance.

A damper for the medium to be treated and flowing from one treatment chamber K2-K4 to the next is located between each two successive treatment chambers K1-K2, K2-K3, K3-K4, where the nozzle channel 52 forms the connection channel. This damper device causes a pressure increase in the medium due to a backup of the medium and admits the medium onto the nozzles 50 at a predetermined pressure, such that the medium can be injected into the respective treatment chamber K2, K3, K4 with a high acceleration and a high velocity. In the present exemplary embodiment, a respective nozzle 50 is designed as a damper device at its medium inlet side, which can be achieved through a suitable shape of the nozzle.

As is also apparent from FIG. 15, the nozzle channel 52 of a nozzle 50, which forms the respective connection channel and narrows in the output direction, has an arched design or features arched or parabolically curved nozzle channel walls.

In addition, a respective nozzle 50 is provided with a small point of discontinuity (not recognizable in the Figures) that generates small high-frequency turbulences in the medium as it exits the nozzle 50. The point of discontinuity may be a separation edge or ridge at the nozzle outlet, an asymmetric nozzle outlet or a vibrating nozzle tongue. When using a vibrating nozzle tongue, its vibration may be caused passively (e.g., using resonance effects caused by the flowing medium) or actively (e.g., by a drive). The small high frequency turbulences reduce friction of the flowing medium on the walls of the treatment chambers K2-K4 similar to the so-called shark skin effect, which can avoid excessive pressure losses inside the treatment chambers K2-K4. This is important because the defined backup of the medium for admitting pressure to the nozzles 50 is to be created by the nozzle channels 52 that function as connection channels and should not be reduced by an unduly great friction-caused pressure loss.

If the medium to be treated is water, the nozzles of the device subject to the invention according to the seventh embodiment affect an additional positive effect. As is generally known, water molecules have a tendency to form clusters at static pressures, e.g., in water pipes, which reduces the solubility characteristics of water. The clusters of the water molecules are reduced in size through the mechanical forces of the nozzle effect, which restores the natural solubility characteristics of water.

The invention is not limited to the exemplary embodiments mentioned above, which serve only the general explanation of the core concept of the invention. Within the scope of protection, the device subject to the invention may also assume different design embodiments as the ones described concretely above. For example, the treatment chambers may also be transparent, exhibit UV-transmissive separating layers, which exhibit different permeabilities or transmission properties for different UV radiation spectra or partial spectra, respectively. Even though natural or synthetic quartz glass was used for the separating layers in the examples above, fundamentally it is also possible to use other UV-transmissive materials if they exhibit the properties for the respective wavelength range of the UV radiation described above. Depending on the application, the number of treatment chambers may vary but is a minimum of two.

The transparent, UV-transmissive turbulence elements 28 that are designed as optical lenses or light conductors may also be shaped such that they unfold their desired optical effects at radiations coming in from both sides of a separation plane. In this manner, the device cannot only be equipped with one central UV radiation source, but also, for example, with additional UV radiation sources placed around the respective treatment chambers and achieve the desired effects described above.

In addition to or alternatively to the above exemplary embodiments according to FIGS. 10 to 11, a transparent, UV transmissive separating layer can also exhibit areas that are designed as optical lenses or light conductors. These areas must not necessarily form the turbulence elements 28 as well or function as such. Of course, this variation can also be realized in combination with the transparent and UV-transmissive turbulence elements that are used as optical lenses and/or as light conductors described above.

There has thus been shown and described a novel device for the treatment of a liquid or gaseous medium using UV radiation which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A device for the treatment of a liquid or gaseous medium using UV radiation, said device comprising, in combination:
   (a) an elongate UV radiation source arranged in an axial longitudinal direction and providing radiation (R) with a wavelength in the at least one of the UVC and UV range in a substantially radial direction of irradiation;
   (b) a plurality of layers of transmissive treatment chambers (K1-K4), serially arranged one on the other in the radiation direction (R);
   (c) a plurality of transmissive separating layers (T1-T4) that separate the UV-transmissive treatment chambers (K1-K4) from each other;
   (d) an upper cover and a lower cover, between which are located the UV radiation source and the separating layers (T1-T4); and
   (e) an exposure time prolongation device, at least a portion (D1-D3) of which is located in at least one of said upper and lower covers;
   wherein, beginning with a first treatment chamber (K1) adjacent to the UV radiation source, said chambers form a flow channel for the medium running in the longitudinal direction of the UV radiation source, said flow channel emptying into the subsequent treatment chamber (K2, K3, K4) further from the UV radiation source in the direction of irradiation (R); and
   wherein a portion of the exposure time prolongation device that is located in at least one of the covers includes a turbulence device (D1-D3) for the medium to be treated.

2. A device as set forth in claim 1, wherein the UV radiation source exhibits a UV radiation spectrum with a wavelength from at least 180 nm to at least 254 nm.

3. A device as set forth in claim 1, wherein the plurality of layers of treatment chambers (K1, K4) are arranged in the radial direction (R) around the UV radiation source.

4. A device as set forth in claim 1, wherein the plurality of layers of treatment chambers (K1-K4) are arranged concentric around the UV radiation source.

5. A device as set forth in claim 1, wherein at least one of the treatment chambers (K1-K4) of the several layers of treatment chambers (K1-K4) extends helically around the UV radiation source.

6. A device as set forth in claim 1, wherein, beginning at the UV radiation source in the direction of irradiation (R), at least the first one (T1) of the transparent, UV-transmissive separating layers (T1-T4), which is located between the UV radiation source and the first treatment chamber (K1) and which is closest to the UV radiation source is made of a first separating layer material that exhibits a UV transmittance that is essentially transmissive to the entire UV radiation spectrum of the UV radiation source, including a first partial spectrum with wavelengths below 200 nm.

7. A device as set forth in claim 6, wherein at least one more (T2) of the separating layers (T1-T4), which follows the first separating layer (T1) in the direction of irradiation (R), is made of the first separating layer material.

8. A device as set forth in claim 7, wherein the overall thickness, measured in the direction of irradiation (R), of a partial layer formed by the one or more separating layers (T1, T2) of a first separating layer material and by one or more treatment chambers (K1, K2) into which the UV radiation enters through the first separating layer material, corresponds essentially to the maximum penetration depth of the first partial spectrum of the UV radiation, said penetration depth being a factor of the absorbability of the medium to be treated and the UV transmittance of the first separating layer material for the first partial spectrum.

9. A device as set forth in claim 7, wherein at least one more (T3, T4) of the separating layers (T1-T4), which follows in the direction of irradiation a separating layer (T1, T2) and is made of the first separating layer material, is made of a second separating layer material that has a UV transmittance, which allows from the UV radiation spectrum of the UV radiation source only a UV radiation at a second partial spectrum with wavelengths greater or equal to 200 nm to pass through.

10. A device as set forth in claim 1, further comprising an exposure time prolongation device for prolonging the exposure time of the medium to be treated in the radiation area of the UV radiation source.

11. A device as set forth in claim 10, wherein the exposure time prolongation device includes a supply channel for the medium to be treated that empties essentially tangential into the first treatment chamber (K1) with regard to the direction of irradiation and provides the medium to be treated with a rotation.

12. A device as set forth in claim 11, wherein the exposure time prolongation device includes an outlet channel for the medium to be treated that essentially protrudes tangentially or in the direction of the rotation with regard to the direction of irradiation (R) from the last treatment chamber (K4), which is located furthest from the UV radiation source in the direction of irradiation (R).

13. A device as set forth in claim 10, wherein the exposure time prolongation device exhibits turbulence elements that are located in device components, which are selected from a group of device components consisting of the treatment chambers (K1-K4), the supply channel, the outlet channel, and the inlet or outlet openings between successive treatment chambers (K1-K4).

14. A device as set forth in claim 10, wherein the successive treatment chambers (K1-K4) form a part of the exposure time prolongation device.

15. A device as set forth in claim 1, wherein the last of the treatment chambers (K4) includes a UV reflection device at its side that is furthest from the UV radiation source in the direction of irradiation.

16. A device as set forth in claim 13, wherein the turbulence elements of the exposure time prolongation device are made transparent and UV-transmissive.

17. A device as set forth in claim 16, wherein the transparent and UV-transmissive turbulence elements are components of a transparent, UV-transmissive separating layer (T1; T2; T3, T4).

18. A device as set forth in claim 16, wherein the transparent and UV-transmissive turbulence elements are each designed as optical lenses.

19. A device as set forth in claim 16, wherein the transparent and UV-transmissive turbulence elements are designed as optical light conductors.

20. A device as set forth in claim 16, wherein at least one of the transparent, UV-transmissive separating layers (T1; T2; T3, T4) exhibits areas that are designed as an optical lens.

21. A device as set forth in claim 13, wherein three-dimensionally formed areas of a transparent, UV-transmissive separating layer (T1; T2; T3, T4) form the transparent, UV-transmissive turbulence elements that are designed as at least one of optical lenses and light conductors.

22. A device as set forth in claim 21, wherein at least one of an optical outlet plane and inlet plane of a turbulence element of a first separating layer, where said turbulence element is designed as an optical lens, is located at a distance from an optical inlet plane and outlet plane, respectively, of a turbulence element of a subsequent second separating layer in the direction of irradiation, wherein said turbulence element is designed as an optical lens, with said distance being less or equal to a distance that is selected from a group of distances consisting of equal to 10 mm, less or equal to 9 mm, less or equal to 8 mm, less or equal to 7 mm, less or equal to 6 mm, less or equal to 5 mm, less or equal to 4 mm, less or equal to 3 mm, less or equal to 2 mm, less or equal to 1 mm, less or equal to 0.5 mm, and less or equal to 0.25 mm.

23. A device as set forth in claim 22, wherein the optical inlet plane and outlet plane, respectively, of a turbulence element of a separating layer located distal from the UV radiation source in the direction of irradiation (R) and designed as a lens is located proximal at a distance from the optical outlet plane and inlet plane, respectively, of a separating layer which is less or equal to a distance that is selected from a group of distances consisting of equal to 10 mm, less or equal to 9 mm, less or equal to 8 mm, less or equal to 7 mm, less or equal to 6 mm, less or equal to 5 mm, less or equal to 4 mm, less or equal to 3 mm, less or equal to 2 mm, less or equal to 1 mm, less or equal to 0.5 mm, and less or equal to 0.25 mm.

24. A device as set forth in claim 1, wherein at least one of the covers includes at least one of an inlet and an outlet, which is connected to at least a first of the treatment chambers (K1-K4), for the medium to be treated.

25. A device as set forth in claim 1, wherein the covers each exhibit a centering device (D1-D3) for the UV-transmissive separating layers (T1-T4) located between them.

26. A device as set forth in claim 1, wherein at least one of the covers includes at least one connection channel that connects a respective treatment chamber (K1-K3) with the respective successive treatment chamber (K2-K4).

27. A device as set forth in claim 26, wherein the turbulence device is integrated in the at least one connection channel.

28. A device as set forth in claim 1, wherein the turbulence device exhibits a nozzle device (D1-D3) with at least one nozzle.

29. A device as set forth in claim 28, wherein the nozzle exhibits a nozzle outlet opening that empties into a treatment chamber (K1-K4), wherein said outlet opening defines an output direction of the medium to be treated with regard to the direction of irradiation (R) of the UV radiation source at an oblique or tangential angle and that causes the medium that flows into the respective treatment chamber (K2-K4) to rotate.

30. A device as set forth in claim 29, wherein the nozzle outlet openings and the output directions of the nozzles of two successive treatment chambers (K1-K2; K2-K3; K3-K4) are oriented in opposite directions to one another such that the direction of rotation of the medium reverses as the medium transitions from one treatment chamber to the next.

31. A device as set forth in claim 1, further comprising at least one nozzle which exhibits a nozzle outlet opening with a point of discontinuity that places the medium flowing from the nozzle into high-frequency turbulence.

32. A device as set forth in claim 1, further comprising a plurality of nozzles (D1-D3) disposed between two respective successive treatment chambers (K1-K2, K2-K3; K3-K4) and arranged ring-like around at least one of the longitudinal axis (L) of the treatment chambers (K1-K4) and the longitudinal axis (L) of the UV radiation source.

33. A device as set forth in claim 26, further comprising a damping device, located between two successive treatment chambers (K1-K2; K2-K3; K3-K4) that are connected by the connection channel to one another, for the medium that flows from one treatment chamber to the next, said damping device causing a pressure increase in the medium and admits the medium to be treated onto the turbulence device (D1-D3) at a predetermined pressure.

34. A method of using the device as set forth in claim 1, said method comprising the steps of UV sterilizing and UV oxidizing a fluid.

35. The method as set forth in claim 34, wherein said fluid is water.

36. The device as recited in claim 6, wherein the first partial spectrum has wavelengths in the range from 200 nm to 180 nm.

* * * * *